United States Patent
Matsuo et al.

(10) Patent No.: US 9,255,883 B2
(45) Date of Patent: Feb. 9, 2016

(54) SURFACE PLASMON-ENHANCED FLUORESCENCE MEASURING APPARATUS

(75) Inventors: Masataka Matsuo, Hachioji (JP); Yukito Nakamura, Tokorozawa (JP); Naoki Hikage, Hachioji (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 13/499,760

(22) PCT Filed: Sep. 25, 2010

(86) PCT No.: PCT/JP2010/066609
§ 371 (c)(1),
(2), (4) Date: Apr. 2, 2012

(87) PCT Pub. No.: WO2011/043202
PCT Pub. Date: Apr. 14, 2011

(65) Prior Publication Data
US 2012/0201716 A1  Aug. 9, 2012

(30) Foreign Application Priority Data
Oct. 5, 2009  (JP) .................................. 2009-231226

(51) Int. Cl.
| G02B 26/10  | (2006.01) |
| G02B 26/00  | (2006.01) |
| G01N 21/55  | (2014.01) |
| G01N 21/552 | (2014.01) |
| G01N 21/64  | (2006.01) |
| G01N 21/89  | (2006.01) |

(52) U.S. Cl.
CPC .............. *G01N 21/648* (2013.01); *G01N 21/55* (2013.01); *G01N 21/553* (2013.01); *G02B 26/00* (2013.01); *G02B 26/10* (2013.01)

(58) Field of Classification Search
None
See application file for complete search history.

(56) References Cited

U.S. PATENT DOCUMENTS

| 2006/0001884 A1 | 1/2006 | Tani |
| 2006/0017931 A1* | 1/2006 | Kimura .......................... 356/445 |
| 2006/0170918 A1 | 8/2006 | Nishiuma |
| 2010/0328654 A1 | 12/2010 | Verschuren et al. |
| 2011/0066914 A1 | 3/2011 | Lee et al. |

FOREIGN PATENT DOCUMENTS

| JP | H01267713 A   | 10/1989 |
| JP | 2001-21565 A  | 1/2001  |
| JP | 3294605 B2    | 4/2002  |
| JP | 2004-156911 A | 6/2004  |
| JP | 2005-283560 A | 10/2005 |
| JP | 2006-17648 A  | 1/2006  |

(Continued)

OTHER PUBLICATIONS

International Search Report International Application No. for PCT/JP2010/066609, mailed Nov. 16, 2010, with English translation.
Written Opinion of the International Searching Authority for International Application No. PCT/JP2010/066609.
Office Action for Japanese Patent Application No. 2011-535335, mailed Mar. 11, 2014. English translation attached.
Extended European Search Report corresponding to Application No. 10821873.6-1554/2487481, PCT/JP2010/066609; Date of Mailing: Feb. 19, 2015.
Japanese Office Action corresponding to Application No. 2014-555464; Date of Mailing: Jun. 16, 2015.
Shuenn-Gi Lee, et al. "Architecture Design of QPP Interleaver for Parallel Turbo Decoding" DOI: 10.1109/VETECS.2010.5493793 Conference: Proceedings of the 71st IEEE Vehicular Technology Conference, VTC Spring 2010, May 16-19, 2010, Taipei, Taiwan, pp. 1-5.

*Primary Examiner* — Neil N Turk
(74) *Attorney, Agent, or Firm* — Cantor Colburn LLP (57) ABSTRACT

Provided is an apparatus having a beam geometry changing device that changes the beam geometry of excitation light, and a control device that controls the beam geometry changing device, with favorable precision, which the apparatus performs a resonance angle scan and to detect a target material.

1 Claim, 6 Drawing Sheets

(56) References Cited

FOREIGN PATENT DOCUMENTS

| JP | 2006320014 A | 11/2006 |
|---|---|---|
| JP | 2008-506969 A | 3/2008 |
| JP | 2008-102117 A | 5/2008 |
| JP | 2009-128012 A | 6/2009 |
| JP | 2009-204483 A | 9/2009 |
| WO | 90/05295 A1 | 5/1990 |
| WO | 2004/040272 A1 | 5/2004 |
| WO | 2009001289 A1 | 12/2008 |

* cited by examiner

SURFACE PLASMON-ENHANCED FLUORESCENCE MEASURING APPARATUS

CROSS REFERENCE TO RELATED APPLICATIONS

This is a U.S. national stage of application No. PCT/JP2010/066609, filed on 25 Sep. 2010. Priority under 35 U.S.C. §119(a) and 35 U.S.C. §365(b) is claimed from Japanese Application No. 2009-231226, filed 5 Oct. 2009, the disclosure of which are also incorporated herein by reference.

FIELD OF INVENTION

The present invention relates to a surface plasmon-enhanced fluorescence measuring apparatus based on a principle of Surface Plasmon-Enhanced Fluorescence Spectroscopy (SPFS).

PRIOR ART

Detection of, for example, a minimal analyte in a live body has been carried out based on the principle of Surface Plasmon-Enhanced Fluorescence Spectroscopy (SPFS). The Surface Plasmon-Enhanced Fluorescence Spectroscopy (SPFS) is that under a condition in which a laser light (exciting light) radiated from a light source is subject to attenuated total reflection (ATR) on a metal thin film surface, by creating a compression wave (surface plasmon) on the metal thin film surface, photon of the laser light (exciting light) radiated from the light source can be localized at a vicinity of the metal thin film whereby by exciting a fluorescent material in the vicinity of the metal thin film, the minimal analyte and/or an extremely low condensation analyte is detected.

In recent years, a surface plasmon-enhanced fluorescence measuring apparatus has been developed based on the principle of the above Surface Plasmon-Enhanced Fluorescence Spectroscopy (SPFS), and the technologies thereof are disclosed, for example, in Patent document 1: U.S. Pat. No. 3,294,605 and Patent Document 2: Unexamined Japanese Patent Application Publication No. 2008-102117.

Figure 11:
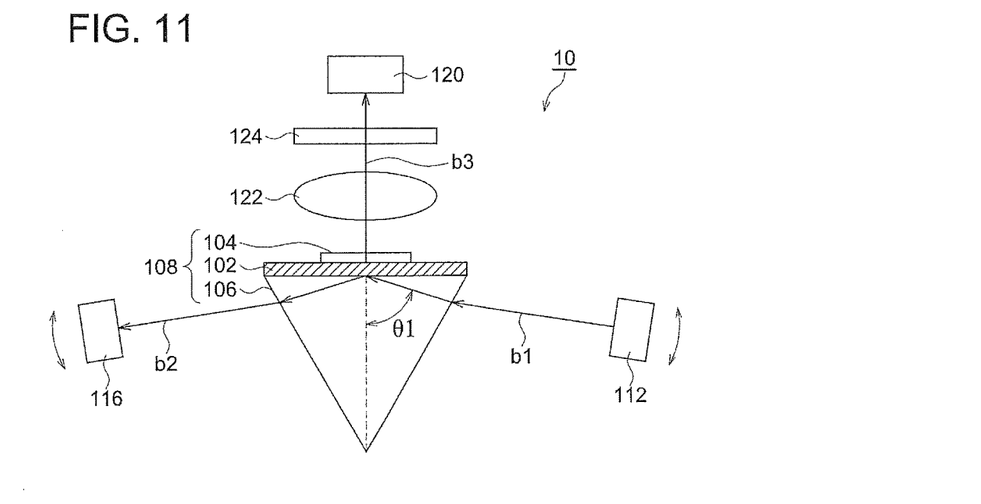
FIG. 11 is a schematic view of a conventional surface plasmon-enhanced fluorescent measuring apparatus.

As FIG. 11 shows, the surface plasmon-enhanced fluorescence measuring apparatus 10 has a basic configuration provided with a chip structural 108 having a metal thin film 102 on a surface of a dielectric member 106 and a reaction layer 104 on a surface thereof.

On the dielectric member 106 side of the chip structural 108 a light source 112 is disposed wherein the exciting light b1 from the light source 112 is introduced into the dielectric member 106 and radiated towards the metal thin film 102, and a light receiving device 116 to receive a metal thin film reflected light b2 which is radiated by the light source 112 and reflected by the metal thin film 102.

On the other hand, on a reaction layer side 104 of the chip structure 108, there is disposed a light detection device 120 to received fluorescent light b3 emitted from a fluorescent substance which has labeled the analyte.

Incidentally, between the reaction layer 104 and the light detection device 120, a light collection member 122 to collect the fluorescent light b3 efficiently and a filter 124 to select a necessary fluorescent light by eliminating light other than the fluorescent light b3 are disposed.

To use the surface plasmon-enhanced fluorescence measuring apparatus 10, on a surface of the metal thin film there is immobilized in advance a first antibody to bind specifically to an antigen such as DNA, representing a detection object, included in the analyte. The analyte and a second antibody to bind specifically to the analyte are fed subsequently to the reaction layer 104 in contact with the metal thin film 102, so that the second antibody is trapped on the reaction layer 104. The trapped second antibody along with the analyte is labeled by the fluorescent substance.

The light source 112 radiates the exciting light b1 on reaction layer 104 where the second antibody is the trapped and the exciting light is introduced into the metal thin film 102 with a specific angle (resonance angle) $\theta 1$, whereby a compression wave (surface plasmon) occurs on the metal thin film. Incidentally, when the compression wave (surface plasmon) occurs, the exciting light b1 and electronic oscillation in the metal thin film are coupled then a phenomenon of a light quantity reduction of metal thin film reflection light b2 occurs.

As a pair, the light receiving device 116 and the light source 112 rotate around a radiation area of the metal thin film 102 to change the incident angle to the metal thin film 102. By changing the incident angle, a point at which the signal of the metal thin film reflection light b2 received by a light receiving device 116 is changed (reduced) is found, whereby the resonance angle $\theta 1$ where the compression wave (surface plasmon) occurs can be obtained.

In accordance with the change of the incident angle, the signal of the metal thin film reflection light b2 received by the light receiving device 116 changes (reduces). Corresponding to the reduction of the light quantity, the compression wave (surface plasmon) occurs locally at the vicinity of the metal thin film. When this occurs, an incident angle at which the light quantity is minimized or an angle near the above incident angle is obtained as the resonance angle $\theta 1$.

By the above phenomenon of occurrence of the compression wave (surface plasmon), the fluorescent substance of the reaction surface 104 on the metal thin film 102 is effectively exited, whereby the light quantity of the fluorescent light b3 emitted by the fluorescent substance increases.

The enhanced fluorescent light b3 is received by the light detection device 120 thought a converging member 122 and a filter 124, whereby the analyte of infinitesimal quantity or extremely low concentration can be detected.

As above, the surface plasmon-enhanced fluorescence measuring apparatus 10 is a high-sensitive measuring sensor capable of observing microscopic molecular activity particularly among biological molecules.

PRIOR ART DOCUMENT

Patent Document

Patent Document 1: U.S. Pat. No. 3,294,605
Patent Document 2: Unexamined Japanese Patent Application Publication No. 2008-102117

DISCLOSURE OF THE INVENTION

Problems to be Solved by the Invention

In a scanning process where the incident angle of the exciting light with respect to the metal thin film 102 is changed to obtain the resonance angle, the radiation area of the exciting light is preferred to be inside of a reaction area of the reaction layer 104. On the other hand, in a detection process to detect the analyte by radiating the exciting light, it is preferred that the entire reaction area is irradiated so as to capture a signal from the labeling agent with a high sensitivity. Therefore, it was difficult to satisfy both of them.

The present invention has one aspect to solve the above problems and an object of the present invention is to perform both of the resonance angle scanning and the detection of the labeled substance with high accuracy.

Means to Solve the Problems

The above object is achieved by the followings.
1. A surface plasmon-enhanced fluorescence measuring apparatus which, by radiating an exciting light on one side of a metal thin film so as to enhance an electric field on the metal thin film, excites a fluorescent substance on a reaction layer formed on another side of the metal thin film and, by a detection device, detects an enhanced fluorescent light from the excited fluorescent substance, the surface plasmon-enhanced fluorescence measuring apparatus, comprising: a beam geometry changing section to change a beam geometry of an exciting light; and a control section to control the beam geometry changing section,
2. The surface plasmon-enhanced fluorescence measuring apparatus of item 1, wherein the control section controls the beam geometry changing section so as to change the beam geometry of the exciting light so as to magnify or reduce a radiation area of the exciting light with respect to the metal thin film, wherein the radiation area in a detection process to detect the fluorescent substance is greater than the radiation area in a resonance angle scanning process to detect a resonance angle.
3. The surface plasmon-enhanced fluorescence measuring apparatus of item 2, wherein the radiation area in the resonance angle scanning process occupies a part of a reaction layer area and the radiation area in the detection process occupies the reaction layer area.
4. The surface plasmon-enhanced fluorescence measuring apparatus of item 2 or 3, further comprising a flow path in which an analyte solution and a reagent solution including the fluorescent goods sent to the reaction layer, wherein the control section controls in a way that the radiation area of the exciting light, which is radiated to detect a fluid sending status in a fluid sending process to send the analyte solution and the reagent solution to the reaction layer, is greater than the radiation area in the detection process.
5. The surface plasmon-enhanced fluorescence measuring apparatus of item 2, further comprising a flow path in which an analyte solution and a reagent solution including the fluorescent goods are sent to the reaction layer, wherein the control section controls the beam geometry changing section so that the radiation area in the resonance angle scanning process occupies a part of a reaction layer area, the radiation area in the detection process coincides with the reaction layer area and the radiation area in a fluid sending process to send an analyte solution and a reagent solution to the reaction layer occupies a reaction layer area and an outside of the reaction layer area.
6. The surface plasmon-enhanced fluorescence measuring apparatus of any one of item 1 to 5, wherein the surface plasmon-enhanced fluorescence measuring apparatus controls in a way that the beam geometry of the exciting light is changed by the beam geometry changing section in accordance with change of the incident angle so as to cancel change of the radiation area of the exciting light on the metal thin film due to the change of an incident angle of the exciting light into the metal thin film, whereby the radiation area of the exciting light on the metal thin film remains constant.

Effect of the Invention

According to the present invention, by providing the beam geometry changing section to change the beam geometry of the exciting light and the control section to control the above section, the resonance angle scanning and the detection of the labeled substance agent can be accurately preformed.

DESCRIPTION OF THE PREFERRED EMBODIMENTS

Figure 1:
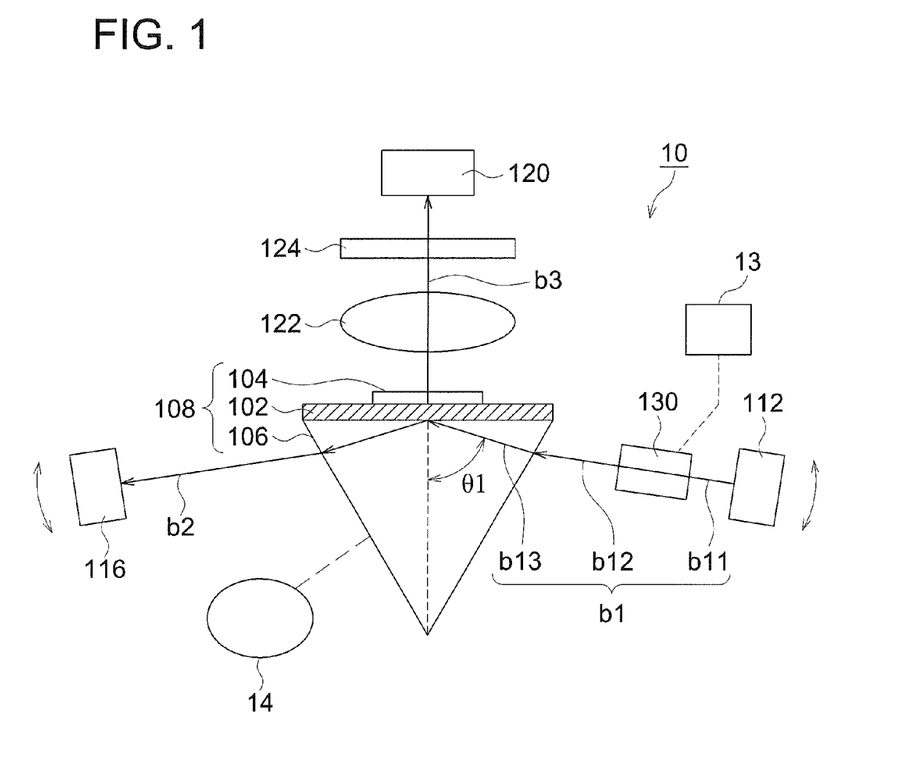
FIG. 1 is a schematic diagram of a surface plasmon-enhanced fluorescent measuring apparatus related to an embodiment.
Figure 2A:
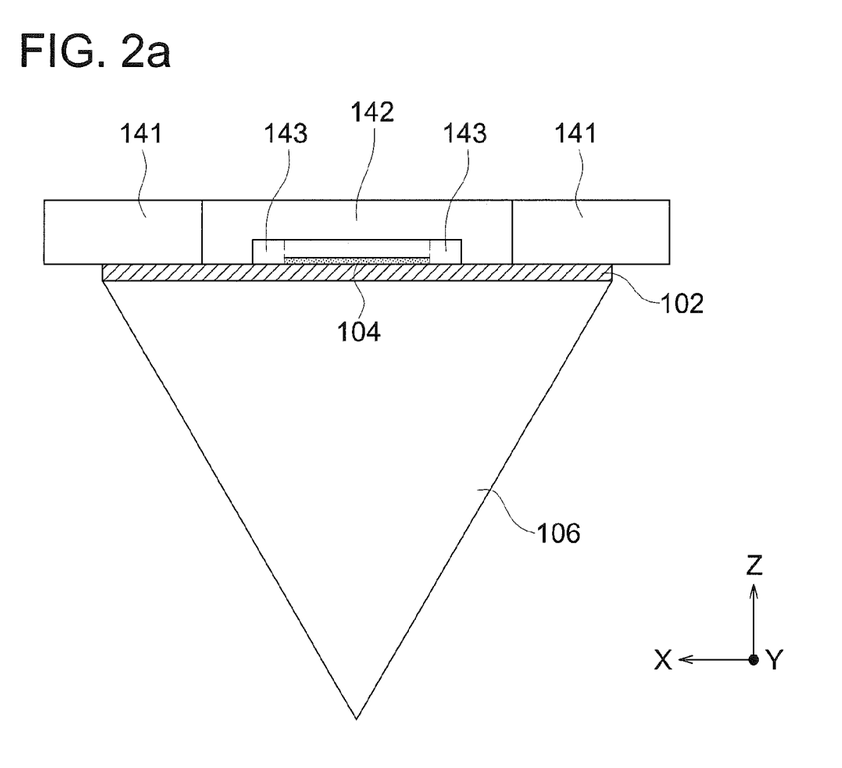
FIG. 2a is across-sectional view of a vicinity of a microchip 14.
Figure 2B:
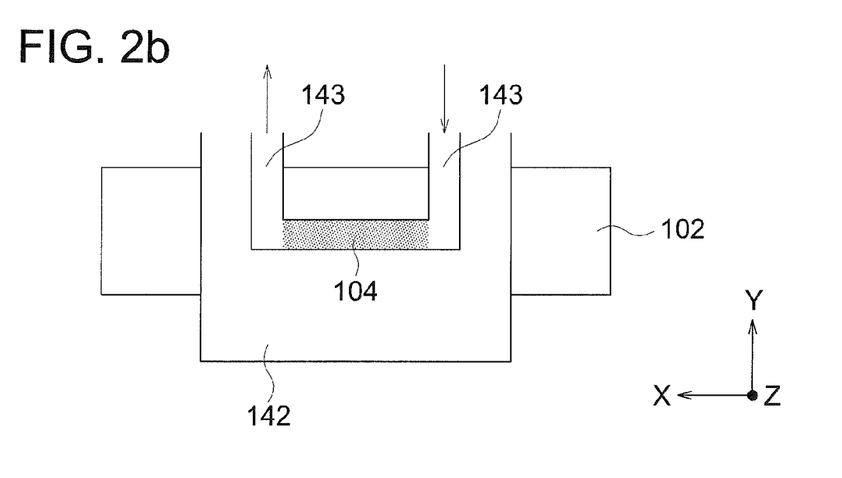
FIG. 2b is a top view of a vicinity of a microchip 14.

The present invention will be described based on the embodiments without being limited thereto.
FIG. 1 and FIG. 2 are schematic views of a surface plasmon-enhanced fluorescent measuring apparatus.
The surface plasmon-enhanced fluorescent measuring apparatus is to detect fluorescent light generated by an excited fluorescent substance by creating a compression wave (surface plasmon) by radiating an exciting light on a metal thin film, thus the surface plasmon-enhanced fluorescent measuring apparatus enables detection of the fluorescent light with an ultrahigh accuracy though the detection sensitivity is increased.

[Surface Plasmon Enhanced Fluorescent Measuring Apparatus 10 and Analyte Detection Method]

As FIG. 1 shows, the surface plasmon-enhanced fluorescent measuring apparatus 10 of the present invention is provided with a chip structure 108 having a metal thin film 102, a reaction layer 104 formed on one surface side of the metal thin film 102 and a dielectric member 106 formed on the other surface side.
On an dielectric member 106 side of the chip structure 108, a light source 112 to emit an exciting light wherein the exciting light is introduced into the dielectric member 106 and radiated towards the metal thin film 102, and a light receiving device 116 to receive a metal thin film reflection light b2 which is the light from the light source 112 reflected by the metal thin film 102.

Figure 7A:
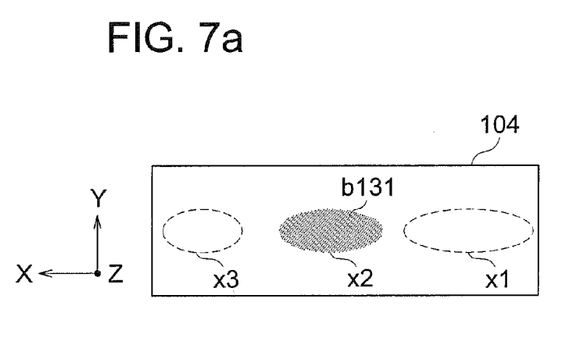
FIG. 7a is a schematic diagram showing a positional relation between an exciting light b13 and a reaction layer 104 in a resonance angle scanning process.

A laser light is preferable as the light radiated from the light source 112 and a gas laser or a solid-state laser having wavelength of 200 to 1000 nm and a semiconductor laser having the wave length of 385 to 800 nm are preferable. Beam geometry of the exciting light b1 radiated from the light source 112 is changed by the beam geometry changing section (also referred to as "beam geometry changing device") 130. Hereinafter, in case the exciting light b1 is distinguished between before and after shape changing by the beam geometry changing section 130, the exciting lights are called exciting light b11 and exiting light b12 respectively. Also, the exciting light passing through the inside of the dielectric member 106 and radiated onto the metal thin film 102 is called an exciting light b13. Further a collective term of the above lights is an exciting light b1. A radiation area on the metal thin film 102 irradiated by the exciting light b13 is called a radiation area b131 (refer to FIG. 7 and so forth). A configuration of the beam geometry changing section 130 will be described later.

On the other hand, on the reaction layer 104 side of the chip structure 108, a light detection device 120 to receive the fluorescent light b3 created in the reaction layer 104 is disposed.

As the light detection device 120, a photomultiplier tube having ultrahigh sensitivity or a CCD image sensor capable of multiple-point measuring is preferable to be used.

The control device 13 is provided with a CPU and a memory. By executing programs stored in the memory each of devices such as the light beam 112, the beam geometry changing section 130, the light receiving device 116 and the light detection device 120 are controlled.

Incidentally, between the reaction layer 104 of the chip structure 108 and the light detection device 120 a converging member 122 to and a filter 124 are disposed. The converging member 122 is to converge the light effectively and the filter 124 is configured to selectively transmit the fluorescent light b3 among the lights by reducing transmission of lights having different wavelength from the fluorescent light b3.

As the converging member 122, discretional converging system can be used as far as the fluorescent signal can be converged efficiently on the light detection device 120. As a simple converging system, an object lens marketed to be used in a microscope can be used. The magnification of the object lens is preferred to be 10 to 100.

On the other hand, as a filter 124 an optical filter and a cut filter can be used. As the optical filter, a natural density filter (ND filter), a diaphragm lens are cited. Further a the cut filter, for example, a dichroic filter and color filter are cited, which removes various kinds of noises such as outside light (illumination light outside the apparatus), exciting light (transmissive element of the exciting light), stray light (scattering element of the exciting light at various portions), scattering light of the plasmon (scattering light originated from the light source caused by the structure or foreign maters on a surface of the plasmon exciting sensor) and self fluorescence of enzyme fluorescent substance.

In the analyte detection method using the above surface plasmon-enhanced fluorescent measuring apparatus 10, a SAM (Self-Assembled Monolayer) to which a first antibody is coupled or a polymer film are provided on a surface of the metal thin film on a side in contact with the reaction layer 104. The first antibody is couple on one surface of the Self-Assembled Monolayer film or the polymer film, and on the other surface of the Self-Assembled Monolayer or the polymer film is fixed onto a surface of the metal thin film 102 directly or indirectly. As the Self-Assembled Monolayer film, for example, a film formed by substituted aliphatic thiol such as $HOOC-(CH_2)_{11}-SH$, and as the polymer material, for example, polyethylene glycol and MPC polymer are cited. The above materials can be prepared at the point of use or a substrate formed by coupling the above materials in advance can be used. Also, a polymer having reactive group (or functional group substitutional for reactive group) reacting with the first antibody can be immobilized on the substrate directly then the first antibody can be immobilized thereon. When coupling the antibody and the polymer using various kinds of reactive groups, amidation condensation reaction through succinimidyl and addition reaction through maleimide are popular.

In a solution "sending process", a solution (hereinafter called analyte solution as well) containing an antigen of an analyte representing a target substances and a reagent solution containing a secondary antibody are sent to the reacting layer 104 configured as above. The antigen can be trapped by the immobilized first antibody. Further, by reacting the reagent solution containing the secondary antibody labeled by the fluorescent substance with the above solution, the trapped antigen is labeled. Incidentally, the secondary antibody can react with the antigen in advance then the first antibody can react with them afterwards.

In the "detection process" to detect the analyte labeled by the fluorescent substance, the light source 112 radiates the exciting light b1 onto the dielectric member 106 having the reacting layer 104 where the analyte is trapped. The exciting light b1 is introduced to the metal thin film 102 at a specific incident angle (resonance angle $\theta 1$) with respect to the metal thin film 102, whereby, the compression wave (surface plasmon) occurs on the metal thin film.

Incidentally, when the compression wave (surface plasmon) occurs on the metal thin film, the exciting light b1 and the electronic oscillation in the metal thin film are coupled and the signal of the metal thin film reflection light b2 is changed (light quantity reduces), whereby a point where the signal of the metal thin film reflection light b2 received by the light receiving device 116 becomes minimum due to change of the signal (reduction of the light quantity) can be found.

By the above compression wave (surface plasmon), the fluorescent substance created in the reaction layer 104 on the metal thin film 102 is effectively excited, whereby a light quantity of the fluorescent light b3 emitted by the fluorescent substance increases. By the light detection device 120 to receive the fluorescent light b3 via the converging member 122 and the filter 124, the analyte of infinitesimal or extremely low condensation can be detected.

Incidentally, as a material of the metal thin film of the chip structure 108 is preferable to be configured with a metal selected from a group consist of gold, silver, aluminum, copper and platinum and more preferable to be configured with gold and furthermore an alloy of the above metals.

The above metals are suitable for the metal thin film 102 because the electric field enhancement is strengthen by the compression wave (surface plasmon).

As manufacturing methods of the metal thin film 102, for example, a spattering method, a vapor deposition method (a resistance heat vapor deposition method, an electron beam vapor deposition method and so forth), an electrolytic plating method, and a non-electrolytic plating method are cited. In particular among them the spattering method and the vapor deposition method are preferred since adjustment of metal thin film forming conditions is easy.

Further the thickness of the metal thin film 102 is preferable in the following ranges:
Gold: 5 to 500 nm
Silver: 5 to 500 nm
Aluminum: 5 to 500 nm
Cupper: 5 to 500 nm
Platinum: 5 to 500 nm
Ally of the above metals: 5 to 500 nm
From view point of electric filed enhancement, the following ranges are preferred:
Gold: 20 to 70 nm
Silver: 20 to 70 nm
Aluminum: 10 to 50 nm
Cupper: 20 to 70 nm
Platinum: 20 to 70 nm
Ally of the above metals: 10 to 70 nm The compression wave (surface plasmon) can easily occur if the thickness of the metal thin film falls 102 within the above ranges. As far as the thickness of the metal thin film 102 falls within the above ranges, the size (lateral×longitudinal) of the metal thin film is not limited.

FIG. 2a is a cross-section of the chip structure 108 and FIG. 2b is a partial top view of the chip structure 108. As the figures show, the reaction layer 104 is disposed on a surface layer of the metal thin film 102 and on a lower layer side in a flow path 143 disposed in a quartz substrate 142. The quartz substrate 142 is supported by fixing member 141. A reagent solution consisting of the secondary antibody labeled by the fluorescent substance and an analyte solution consisting of the analyte are sent to the flow path 143 by an unillustrated pump.

As the analyte, blood, serum, plasma, urine, nasal fluid, saliva, feces, and body cavity fluid (spinal fluid, ascites fluid and pleural effusion) are cited. The analyte concluded in the analyte solution is, for example, nucleic acid (single-strand or double strand DNA, RNA, polynucleotide, oligonucleotide, PNA (peptide nucleic acid), nucleotide, nucleotide and molecular modification of nucleotide), protein (polypeptide, and oligopeptide), amino acid (modified amino acid is included), glucide (oligosaccharide, polysaccharide chain and sugar chain), lipid, or molecular modification and complex thereof are cited. Specifically, the analyte can be carcinoembryonic antibody such as AFP (a fetoprotein), tumor marker, signal transducer and (a) hormone without being limited thereto.

The fluorescent substance is not limited as far as the substance emits fluorescent light b3 by being irradiated by a predetermined exciting light b1 or by using a field effect. The fluorescent light b3 in the present Specification includes various kinds of luminescence such as phosphorescence.

As the dielectric member 106, a prism having an angle of 60 degree with a high deflective index can be used. As a high deflection material, various kinds of transparent inorganic substances, natural polymers and synthetic polymers can be used. From the view points of chemical stability, manufacturing stability and optical transparency, silica dioxide (SiO2), titanium dioxide (tiO2), polycarbonate (PC), cycloolefin polymer (COP), and optical polyester (OKP: manufactured by Osaka Gas Chemical Co., Ltd.) can be used.

The above surface plasmon-enhanced fluorescent measuring apparatus 10 has an angle changing section (unillustrated) to adjust an optimum angle (resonance angle θ1) for surface plasmon resonance by the exciting light b1 to be radiated on the metal thin film 102 from the light source 112.

Here, the angle changing section (unillustrated) controlled by the control device 13 is able to change the angle in the range of 45 to 85° by rotation via a servo motor of the angle changing section around an radiation area synchronized with the light receiving device 116 and the light source 112 to seek conditions of attenuated total reflection (ATR) in the "resonance angle scanning process". A resolution thereof is preferred to be not less than 0.01°.

[Beam Geometry Modification Section]

Figure 3:
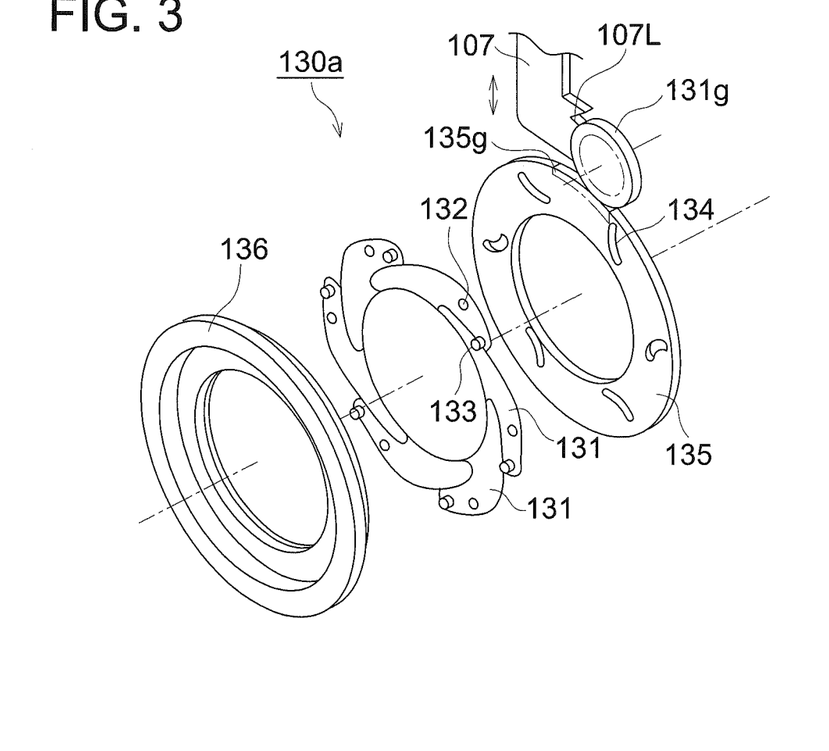
FIG. 3 is a schematic diagram showing a beam geometry changing section 130b using a diaphragm mechanism.
Figure 4:
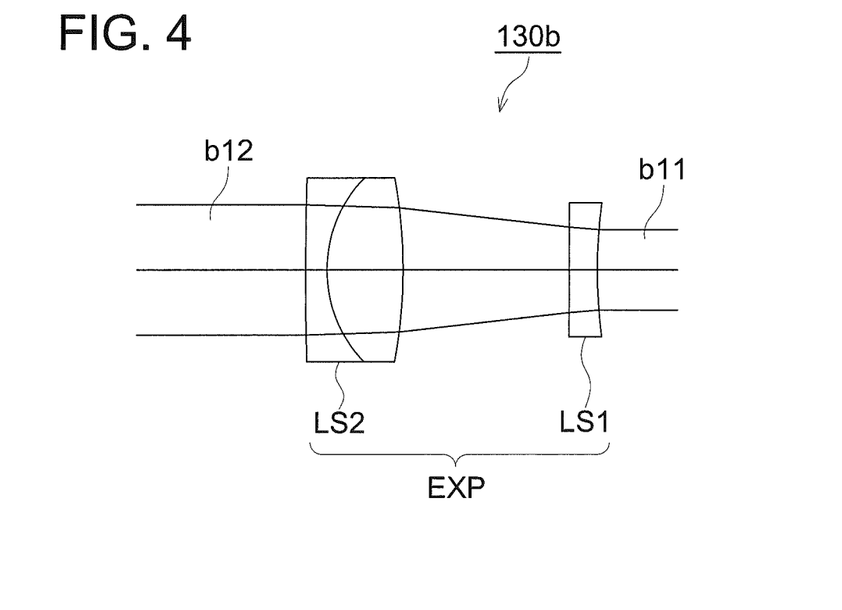
FIG. 4 is a schematic diagram showing a beam geometry changing section 130b using a beam expander.
Figure 5:
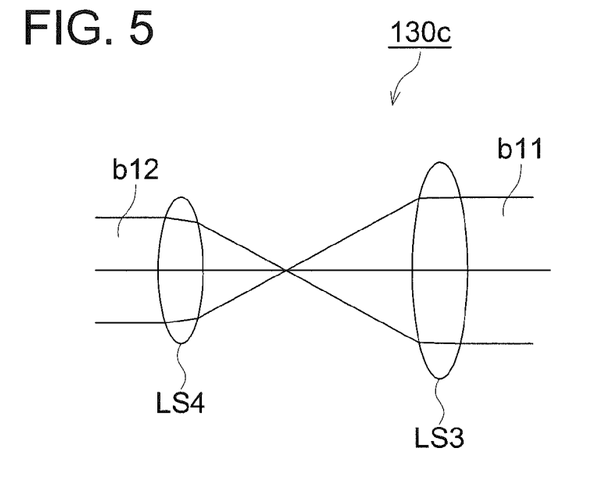
FIG. 5 is a schematic diagram showing a beam geometry changing section 130b using a zoom lens.

FIG. 3 to FIG. 5 are schematic diagrams showing examples of beam geometry changing sections 130. In the present invention, meaning of beam the shape changing includes not only changing the geometry of the beam but magnification and reduction of a beam diameter. The beam geometry changing sections 130a, 130b and 130c (the beam geometry changing 130 is a collective term of the above sections) are controlled by the control device 13.

FIG. 3 is a schematic diagram showing the beam geometry changing section 130a using a diaphragm mechanism. In the above figure, a gear wheel 131g is meshed with a rack gear 107L formed on a diaphragm member drive rack 107. The gear wheel 131g is beard by a boss formed at an unillustrated frame. The gear wheel 131a meshes with a gear wheel section 135g formed at an outer circumference of a diaphragm opening/closing ring 135. An axle hole 132 is formed on a diaphragm fin 131 so that the diaphragm fin 131 is rotatably supported by a boss formed on a diaphragm fin supporting ring 136. Also, a pin 133 is implanted on the diaphragm fin so that the diaphragm pin 133 is inserted in a groove section 134 formed on the diaphragm ring 135. With the above configuration, by moving the diaphragm member drive rack 107 in an arrow direction in the figure, the diaphragm open/close ring 135 rotates via the gear wheel 131g whereby multiple diaphragm fins 131 rotate around the axis hole 132 to perform an aperture function as an iris diaphragm. The beam geometry changing section 130a can narrow the shape of the exciting light b1 radiated from the light source 112. Incidentally, in the example shown in FIG. 3, while the exciting light b1 is narrowed in a shape of a circle centering around the light axis, the exciting light b1 can be narrowed in a shape of a square centering around the light axis with four or two diaphragm fins 131.

FIG. 4 is a schematic diagram showing the beam geometry changing section 130b using a beam expander. In FIG. 4, the beam geometry changing section 130b to serve as the beam expander is configured with a first lens LS1, a second lens LS2 formed by jointing a positive lens and a negative lens. In the beam geometry changing section 130b in FIG. 4, by moving at least the first lens or the second lens in the light axis direction via an unillustrated lens moving device, a beam diameter of the exciting light b11 radiated form the light source 112 can be changed.

FIG. 5 is a schematic diagram showing a beam geometry changing section 130c using a zoom lens. In FIG. 5, the beam geometry changing section 130c, to serve as a zoom lens, configured with a first lens LS3 and a second lens LS4 having a shorter focal length than that of the first lens LS3, can change the beam diameter with be a predetermined magnification percentage or a reduction percentage in accordance with the ratio of the focal length. Incidentally, there can be a configuration that one of the above lenses is configured with a lens group and one lens in the lens group is moved in the light axis direction by a moving mechanism, wherein the magnification and reduction percentages can be changed by changing the focal length of the lens group.

Also, the beam geometry changing section 130 can be a combination of configurations in FIG. 3 and FIG. 5. Also in FIG. 4 and FIG. 5, while a spherical lens is used, a cylindrical lens can be used to change the magnification and reduction percentages. The configurations of the beam geometry changing section shown in FIG. 3 to FIG. 5 are examples without the present invention being limited thereto and the other configurations to change the beam geometry capable of changing the cross-sectional area, the beam diameter, and the beam geometry can be used.

[Beam Geometry Control Flow]

Figure 6:
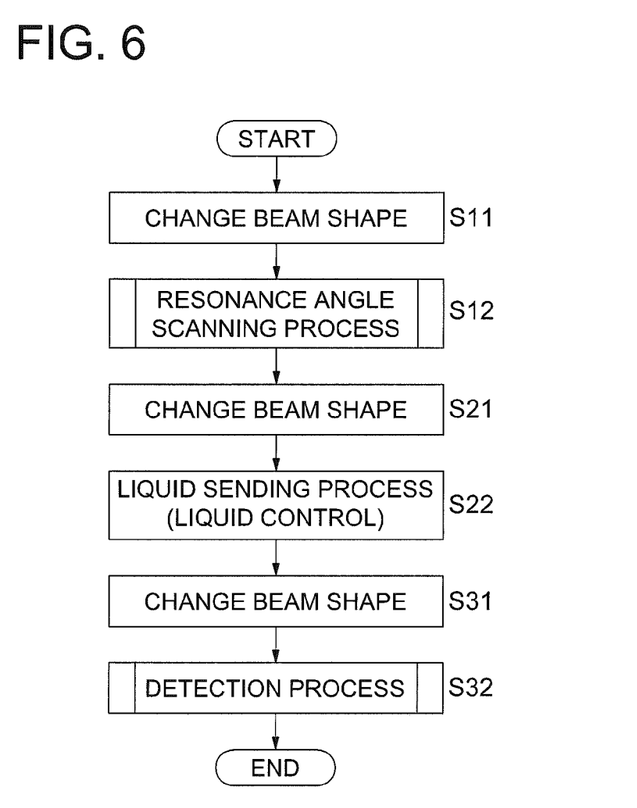
FIG. 6 shows a flow chart showing a control flow executed by the control device 13.

Control of beam geometry changing will be described with reference to the FIG. 6 to FIG. 8. FIG. 6 is a flow chart showing a control flow executed by the control device 13.

[Beam Geometry in Resonance Angle Scanning Process]

In Step S11 in FIG. 6, the beam geometry changing section 130 conducts geometry changing with respect to the exciting light b1 so that the beam geometry becomes a desired beam geometry set in advance. In Step S12, the resonance angle scanning process is executed with the beam geometry changed in Step S11. Here, the beam geometry changed in Step S11 is an optimum beam geometry for the resonance angle scanning process, which will be described with reference to FIG. 7.

Figure 7B:
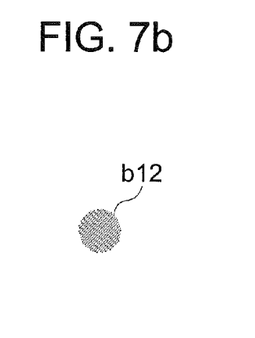
FIG. 7b is a schematic diagram showing a cross-sectional shape of the exciting light b12 after beam geometry changing in the resonance angle scanning process.

FIG. 7a is a schematic diagram showing a positional relation between a reaction layer 104 and a radiation area b131 by the exciting light b13 on the metal thin film 102 in the resonance angle scanning process, and FIG. 7b is a schematic diagram showing a cross-sectional shape of the exciting light b12 after beam geometry changing in the resonance angle scanning process. As mentioned above, in the resonance angle scanning process executed in Step S12, the incident angle to the metal thin film 102 swings while synchronizing the light receiving device 116 and the light source 112, so as to seek an incident angle (positions of the light receiving device 116 and the light source 112) where attenuated total reflection occurs.

The resonance angle θ1 changes with a chemical condition of the surface of the metal thin film 102. In order to obtain the resonance angle θ1 with accuracy in the resonance angle scanning process, the exciting light b13 has to be radiated on an area of the reaction layer 104 where the first antibody is immobilized on the surface of the metal thin film 102. Because in case the exciting light b13 is radiated in a way that the radiation area b131 locates partially or totally at outside the reaction layer 104 on the metal thin film 102, the resonance angle θ1 can not be obtained accurately. In the present embodiment, the beam geometry of the exciting light b12 is optimized in advance by the beam geometry changing section 130 so that the radiation area b131 of the exciting light b13 falls within the area of the reaction layer 104 in a changing range of the incident angle in the resonance angle scanning process.

In the present embodiment, (1) The metal thin film 102 is formed on a surface of the dielectric member having the refraction index of n=1.515. The dielectric member 106 is a prism of 60° and 25 mm on a side. A size of the reaction layer 104 is 1.0 mm (Y direction)×3.0 mm (X direction). (2) The exciting light b1 is a laser light having a wavelength of 633 nm. A scanning range of the incident angle of the exciting light b1 into the metal thin film 102 in the resonance angle scanning process is 79°±3°. The incident angle referred here is an incident angle where refraction by introducing into the dielectric member does not occur. Hereinafter, when the term of "incident angle" is used simply, it means the above mentioned incident angle. The incident angle of exciting light b13 into the metal thin film 102 after the optical path is bent on the surface of the dielectric member 106 in the incident angle of 79°±3° is 70.48° to 74.32° in calculation.

In FIG. 7a the radiation area b131 of the exciting light b13 at incident angles 82°, 76° and 79° which are an upper limit, a lower limit and an intermediate of scanning range are denoted by x1, x3 and x2 respectively. As FIG. 7a shows in accordance with change of the incident angle, the size of and the radiation position of the radiation area b131 of the exciting light b13 on the surface of the metal thin film 102 change.

In the present embodiment, in the scanning rage of the incident angle in order that the radiation area b131 of the exciting light b13 falls within the area (1.0×3.0 mm) of the reaction layer 104, it is calculated that the shape of the exciting light b12 is adequate to be a circle of 40.3 mm. In Step S11, the control device 13 controls the beam geometry changing section 130 to conduct geometry changing to achieve the above geometry. Incidentally, with respect to the exciting light b12 of ϕ0.3 mm, the size of the radiation area b131 of the exciting light b13 on the surface of the metal thin film 102 is 1.161 mm (X direction diameter) at x1(82°), and 0.918 mm (X direction diameter) at x3(76°).

Other Embodiment

As above, in accordance with change of the incident angle of the exciting light, the size and the radiation position of the radiation area b131 of the exciting light b13 on the surface of the metal thin film changes. In another example it is possible to control that the size of the radiation area b131 of the exciting light b13 on the metal thin film surface 102 remains constant by changing the geometry of the beam of the exciting light b12 via the beam geometry changing section 130 in accordance with change of the incident angle so as to cancel the change of the size. For example, in case the incident angle is changed in the range from x1(82°) to x3(76°), the beam geometry of the exciting light b12 is changed in accordance with the change of the incident angle so that the diameter in x direction is a constant value of 0.90 mm.

In the above manner, by maintaining the size of the area to be irradiated, an effect due to change of the size of the radiation area with respect to the light quantity of the fluorescent light b3 can be inhibited.

[Beam Geometry in Fluid Sending Process]

In the fluid sending process, as described in the forgoing, the analyte solution and the reagent solution including the second antibody labeled by the fluorescent substance are sent to the reaction layer 104. As mentioned above, since the first antibody is immobilized on the metal thin film 102 in contact with the reaction layer 104, by sending the analyte solution and the reagent solution, the antigen included in the analyte solution to specifically react with the first antibody is trapped, and the second antibody to react specifically with the antigen is trapped.

In Step S21 in FIG. 6, the beam geometry change section 130 conducts geometry change with respect to the exciting light b1 so that the beam geometry is changed to be a beam geometry set in advance. In Step S22, using the beam geometry changed in the Step S21, fluid sending control in the fluid sending process is conducted. Fluid sending control is to (detect) observe a condition of fluid sending that whether or not the analyte solution and the reagent solution are sent normally. In fluid sending control, for example, whether or not the fluid is sent normally or whether or not bubbles are created in the flow path or not is detected.

In fluid sending control, besides the reaction layer 104, the flow path 143 at vicinity thereof also has to be observed. In the fluid sending control, the beam geometry has to be set so that the radiation area covers at least entire area of the reaction layer 104 or the radiation area covers the entire reaction layer 104 and an outside thereof. Thus the beam geometry is set in a way that the radiation area (on the metal thin film surface 102) of the fluid sending control (Step S22) is wider than the that of a detection process (Step S32) to be described (Step S21). Whereby, besides the reaction layer 104, the fluid sending condition of the fluid in the vicinity flow path 143 can be controlled.

Incidentally, in the fluid sending, detection is not necessarily via the fluorescent light b3 generated by the surface plasmon on the surface of the metal thin film 102. The detection can be carried out by detecting reflection light or scattering light on the surface of the metal thin film 102 via the light receiving device 116. In the above case, the exciting light b1 does not have to be introduced with the resonance angle θ1. Also, since there can be a problem that by giving a strong energy to the fluorescent substance at a time other than the detection, discoloration of a pigment causes reduction of sensitivity and quantitative accuracy, the detection carried out by the reflection light or the scattering light is more preferable than detection (observation) by the electric filed enhanced by the surface plasmon. The intensity or the wavelength of the exciting light b1 can be changed.

[Beam Geometry in Detection Process]

In Step S31 in FIG. 6, the beam geometry changing section 130 conducts geometry changing with respect to the exciting light b1 so as to form a beam geometry set in advance. In Step S32, using the beam geometry changed in the Step S31, detection process is executed. Here the beam geometry set in Step S31 is an optimum beam geometry for the detection process. The followings are descriptions with reference to FIG. 8.

Figure 8A:
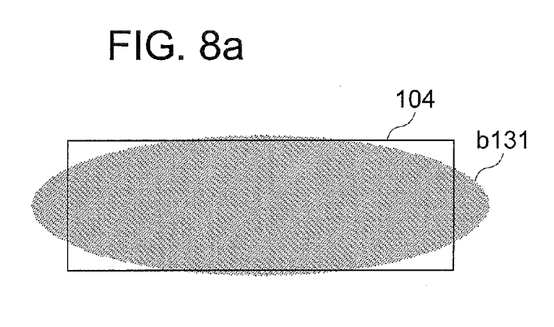
FIG. 8a is a schematic diagram showing a positional relation between an exciting light b13 and a reaction layer 104 in a detection process to detect an analyte.

FIG. 8a is a schematic diagram showing a positional relation between the reaction layer 104 and the radiation area b131 of the exciting light b13 on the metal thin film 102 in the detection process to detect the analyte. FIG. 8b is a schematic diagram showing a cross-section of the exciting light b12 after beam geometry changing in the detection process.

As described above, in the resonance angle scanning process, the size of the exciting light b13 has to be reduced so that the exciting light b13 is not radiated outside the reaction layer 104. On the other hand in the detection process, in order to detect the fluorescent substance, which has labeled the analyte trapped across the entire area of the reaction layer 104, it is preferred that the exciting light b13 is radiated across the reaction layer 104 as wide as possible.

In the present embodiment, the control device 13 controls the beam geometry changing section 130 so that the radiation area of the detection process is wider than that in the resonance angle scanning process. Specifically, in the resonance angle scanning process, a partial area of the reaction layer 104 is irradiated, and the geometry of the exciting light b12 is determined in a way that at the incident angle (resonance angle) into the metal thin film 102 determined in the resonance angle scanning process, the radiation area b131 of the exciting light b13 in the detection process substantially coincides with an entire area of the reaction layer 104 or the radiation area b131 substantially coincides with the area of the reaction layer 104. In FIG. 8b the beam geometry changing section 130 changes the geometry of the cross-section of the exciting light b12 to a circle of Ø10 mm. With the above geometry, as FIG. 8a shows, it is revealed that the radiation area b131 of the exciting light b13 covers most of the reaction layer 104. Incidentally, in accordance with the value of the incident angle (resonance angle) determined in the resonance angle scanning process, the position of the radiation area differs, thus the beam geometry is formed so as to radiate the most of the reaction layer 104 even at the upper and lower limits in the scanning range of the incident angle. Also, it is preferred that with a configuration to move the chip structure 108 in the Z axis direction by the position adjusting mechanism 14 shown in FIG. 1, by adjusting in the Z axis direction via the position adjusting mechanism 14 in accordance with the resonance angle θ1, the center of the radiation area of the exciting light introduced with the resonance angle θ1 coincides with the center of the reaction layer 104.

According to the present embodiment, the control section 13 controls the beam geometry changing section 130 to adequately change the beam geometry of the exciting light, whereby both the resonance angle scanning and the detection of the labeling substance can be accurately conducted.

Exemplary Modification

Figure 8B:
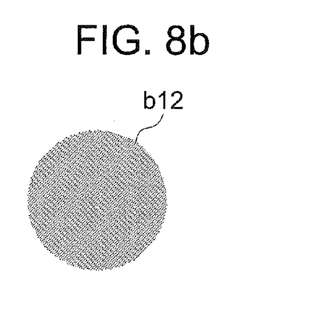
FIG. 8b is a schematic diagram showing a cross-sectional shape of the exciting light b12 after beam geometry changing in the detection process.
Figure 9A:
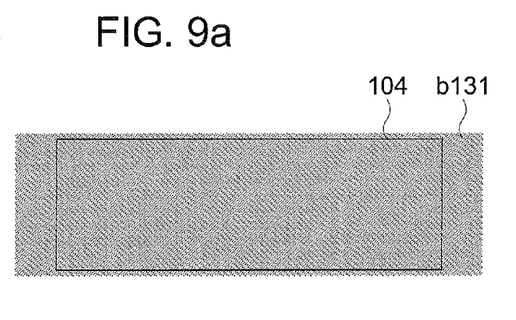
FIG. 9a and FIG. 9b are exemplary modifications of FIG. 8a and FIG. 8b respectively.
Figure 9B:
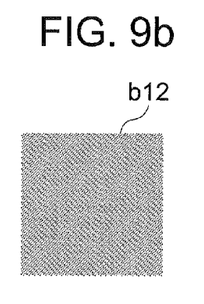

FIG. 9 shows an exemplary modification of one in FIG. 8. In the embodiment shown by FIG. 9, the beam geometry changing section 130 is a diaphragm mechanism shown in FIG. 3, which can form the beam geometry to be a square shape. In the example shown by FIG. 9b, the beam geometry changing section 130 forms the cross-section of the exciting light b12 to be a square 1.0 mm on a side. Whereby, as FIG. 9a shows, in case the reaction layer 104 (reaction area) is an rectangle, by forming the beam geometry similar to the shape thereof the radiation area b131 of the exciting light b13 in the detection process can cover the entire area of the reaction layer 104 easily, and the signals from the fluorescent substance in a wider area than that in FIG. 8 can be detected unfailingly.

Other Embodiment

Figures 10A, 10B:
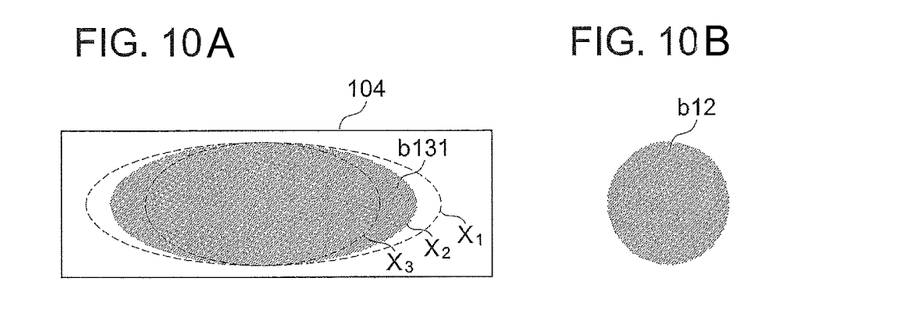
FIG. 10a and FIG. 10b are corresponding to FIG. 7a and FIG. 7b respectively.
Figure 10C:
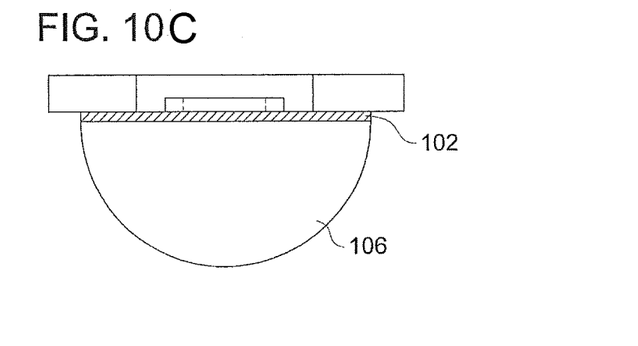
FIG. 10c is an exemplary modification using a dielectric member 106.

FIG. 10a to FIG. 10c show, an embodiment where the dielectric member 106 in a shape of a half circle is used as an exemplary modification. In the embodiment shown by FIG. 10, the radiation position of the exciting light b13 on the metal thin film 102 can be fixed irrespective of the incident angle as described later.

As FIG. 10c shows, in case the dielectric member 106 in the shape of the half circle is used, in the resonance angle scanning process, even if the incident angle is changed by moving the light source 112 and the light receiving device 116, by radiating the exciting light b1 towards the center of the half circle of the dielectric member 106, the exciting light b1 is always radiated onto the surface of the dielectric member 106 form a normal line direction. Whereby, bending of the light path on the surface of the dielectric member 106 does not occur, therefore as FIG. 10a shows, the center of the radiation area b131 of the exciting light b13 on the reaction layer 104 always stays at the same position even if the radiation area b131 is changed as x1 to x3 due to change of the incident angle.

In FIG. 7a considering change of the radiation position of the exciting light b13 and change of size in the radiation area, the beam geometry has been set. However, in the embodiment shown by FIGS. 10a to 10c, change of the size only has to be considered. As a result, as FIG. 10b shows the beam geometry changed by the beam geometry changing section 130 can be set to be a circle of approximately Ø 0.8 mm (dielectric member 106 incident position) whose length in the X direction is extended compared with the one in FIG. 7b. Incidentally, in case the dielectric member 106 in the shape of the half circle is used, the exciting light b12 has to be a diverging light so that the incident light (exciting light b13) inside the dielectric member 106 is a parallel light.

As FIG. 1 shows, in an embodiment in which a triangle dielectric member 106 is used, by interlocking the incident angle and the position of the chip structure 108 calculated from a size and a refraction index of the dielectric member via the position adjusting mechanism 14, the radiation area, which moves in accordance with the incident angle, can be maintained at a center of a reaction place (reaction layer 104), and the beam geometry can be controlled considering only change of the area size of the radiation area of the exciting light due to change of the incident angle.

Further, as the former embodiment and the other embodiments by applying a configuration that the beam geometry changing section 130 changes the beam geometry of the exciting light b12 in accordance with the change of the incident angle of the exciting light, control that the size and the center position of the radiation area b131 of the exciting light b1 on the metal thin film 102 remain constant is possible.

DESCRIPTION OF THE SYMBOLS

10 Enhanced fluorescent measuring apparatus
13 Control device
14 Position adjusting mechanism
130, 130*a*, 130*b* and 130*c* Beam geometry changing section
b1, b11, b12 and b13 Exciting light
b131 Radiation area
b2 Metal thin film reflection light
b3 Fluorescent light
102 Metal thin film
104 Reaction layer
106 Dielectric member
18 Chip structure

What is claimed is:

1. An illumination system, for use with an analyte solution and a reagent solution including a fluorescent substance, the illumination system comprising:
   a metal thin film;
   a reaction layer formed on one side of the metal thin film to which the analyte solution and the reagent solution including the fluorescence substance are sent;
   a light source structured to radiate an exciting light on a side of the metal thin film opposite to the reaction layer so as to enhance an electric field on the metal thin film, whereby the fluorescence substance in the reaction layer is excited, and the radiation of the exciting light on the metal thin film defines a radiation area on the metal thin film;
   a detection device structured to detect an enhanced fluorescent light from the fluorescence substance in the reaction layer; and
   a beam geometry changing device structured to vary a beam geometry of the exciting light in accordance with operation of the illumination system; and
   a control section structured to control the beam geometry changing device during operation of the illumination system;
   wherein the beam geometry changing device comprises one of:
      a diaphragm mechanism comprising diaphragm fins, and a diaphragm fins moving mechanism configured to move the diaphragm fins for varying an aperture, the diaphragm fins moving mechanism being operatively connected with the control section;
      a beam expander comprising a first beam expander lens, a second beam expander lens, and a lens moving device configured to move the first beam expander lens or the second beam expander lens in an axial direction of the exciting light, the lens moving device being operatively connected with the control section; and
      a zoom lens comprising a first zoom lens component, a second zoom lens component, and a moving mechanism configured to move the first zoom lens component or the second zoom lens component in an axial direction of the exciting light, the moving mechanism being operatively connected with the control section, and
   wherein the control section is configured to control the beam geometry changing device to perform one of:
      varying an aperture of the diaphragm mechanism through the diaphragm fins moving mechanism when the beam geometry changing device comprises the diaphragm mechanism;
      moving the first beam expander lens or the second beam expander lens in an axis direction of the exciting light through the lens moving device when the beam geometry changing device comprises the beam expander; and
      moving the first zoom lens component or the second zoom lens component in an axis direction of the exciting light through the lens moving device when the beam geometry changing device comprises the zoom lens.

* * * * *